United States Patent [19]

Hannig et al.

[11] 4,061,560

[45] Dec. 6, 1977

[54] APPARATUS FOR DEFLECTION ELECTROPHORESIS

[75] Inventors: Kurt Hannig, Krailing; Hanns Wirth, Hohenpeissenberg, both of Germany

[73] Assignee: Max-Planck-Gesellschaft zur Forderung der Wissenschaften e.V., Gottingen, Germany

[21] Appl. No.: 662,089

[22] Filed: Feb. 27, 1976

[30] Foreign Application Priority Data

Feb. 28, 1975 Germany .............................. 2508844

[51] Int. Cl.² ............................................ G01N 27/26
[52] U.S. Cl. ............................ 204/299 R; 204/180 R; 204/180 G
[58] Field of Search ............... 204/180 P, 180 R, 299, 204/301

[56] References Cited

U.S. PATENT DOCUMENTS

| 3,412,008 | 11/1968 | Strickler | 204/301 |
| 3,498,905 | 3/1970 | Strickler | 204/299 |
| 3,655,541 | 4/1972 | Strickler | 204/180 R |
| 3,663,395 | 5/1972 | Strickler | 204/180 R |

Primary Examiner—Arthur C. Prescott
Attorney, Agent, or Firm—Spencer & Kaye

[57] ABSTRACT

In a procedure for performing a continuous, free-film deflection electrophoresis in which a narrow stream of a sample mixture is introduced into a thin strip of a buffer solution flowing through a separating chamber while an electric field is applied transversely to the flow direction, band broadening of the sample stream fractions is reduced by providing suitably selected values for the temperature gradient in the chamber and the wall zeta. Additional improvements are achieved by constructing the buffer solution flow path in the region of sample introduction in order to increase the buffer solution velocity thereat.

12 Claims, 14 Drawing Figures

APPARATUS FOR DEFLECTION ELECTROPHORESIS

BACKGROUND OF THE INVENTION

The present invention relates to a method and apparatus for performing a continuous free-film deflection electrophoresis, in which a spatially narrowly constricted stream of a sample mixture which is to be fractionated is introduced into a thin strip of a buffer solution flowing through a separating chamber defined by two plane parallel walls, an electrical voltage is applied to the buffer strip to produce an electrical field therein which extends transversely to the direction of flow and parallel to the walls of the separating chamber, and the separated fractions are detected by an analyzer device disposed downstream of the sample introduction location, the velocity profile of the buffer stream between the separating chamber walls as well as electroosmosis effects as a result of the zeta potential of the separating chamber walls tending to impart a crescent-shaped deformation to the flow cross section of the fraction.

A publication by Allen Strickler and Terry Sacks in "Preparative Biochemistry", Volume 3, No. 3, (1973) pages 269-277, teaches that crescent-shaped deformations of the flow cross section of a given fraction, resulting from the velocity profile of the buffer stream, can be compensated by appropriate setting of the zeta potential of the separation chamber walls so that, for this fraction, the sample stream ribbon can be given a well defined cross section transverse to the flow direction, and thus optimum separation efficiency can be obtained. The setting of the zeta potential in the known arrangement is effected by applying an appropriate coating to the separating chamber walls, for example a pressure-sensitive polyester foil which, if required, may be provided with an additional layer of collodion, agar or gelatin.

SUMMARY OF THE INVENTION

It is an object of the present invention to perform continuous free-film deflection electrophoresis in a manner which permits easy and quick setting of the compensation conditions for optimum separation efficiency without requiring modifications to the apparatus, such as changes in the coating of the separating chamber walls.

A further object of the invention is to improve the introduction of the sample substance and to assure production of a very thin and uniform sample stream ribbon with reproducible properties.

The present invention makes it possible to realize optimum separating efficiency and resolution for a given fraction. Optimization conditions can be quickly set so that it is possible to adjust the apparatus as regards optimum resolution from one fraction of the given sample mixture to another fraction thereof, or to quickly adjust the apparatus to another sample mixture, and high sampling frequency is assured.

These and other objects according to the invention are achieved, in a continuous free-film deflection electrophoresis procedure performed by introducing a spatially narrowly defined stream of a sample mixture which is to be divided into fractions is introduced into a thin layer of a buffer solution steam flowing through a separating chamber, opposite sides of which chamber are delimited by two parallel walls, applying an electrical voltage to the buffer layer to produce an electrical separating field which extends transversely to the direction of flow and parallel to the walls delimiting the separating chamber, and detecting the separated fractions by means of an analyzer device disposed downstream of the point of sample introduction, and in which the velocity profile of the buffer stream between the separating chamber walls and the electroosmosis effects due to the zeta potential of the separating chamber walls tend to deform the flow cross section of the fractions into a crescent shape, by giving the temperature gradient in the buffer layer, which is dependent on the temperature of the separating chamber walls and the Joule heat produced in the buffer layer, the applied electrical voltage, and the conductivity of the buffer solution values, relative to the buffer flow velocity in the separating chamber and the zeta potential of the separating chamber walls, which cause the deformations resulting from the temperature gradient, the flow velocity of the buffer solution and the zeta potential of the separating chamber walls to be substantially compensated in the vicinity of the analyzer device.

The objects according to the invention are further achieved, when the above-described procedure is performed in apparatus composed of a separating chamber arrangement including a separating chamber gap defined by two parallel walls and two electrode chambers disposed to either side of the separating chamber gap and each provided with an electrode, the electrode chambers being separated from the separating chamber gap by an ion transmitting membrane, the apparatus being further provided with a device for introducing a sample into the separating chamber gap, a device for producing a buffer solution flow in the separating chamber gap and a device for analyzing separated fractions of the sample, by providing such apparatus with an arrangement for the controlled introduction of an adjuvant fluid into the buffer solution entering the separating chamber gap.

DESCRIPTION OF THE PREFERRED EMBODIMENTS

As is known, the flow cross section, or flow zone, of a given fraction is influenced transversely to the direction of flow, i.e. parallel to the direction of separation, by the following effects:
a. velocity profile
b. osmosis profile
c. temperature gradient, and
d. diffusion.

Figure 1A:
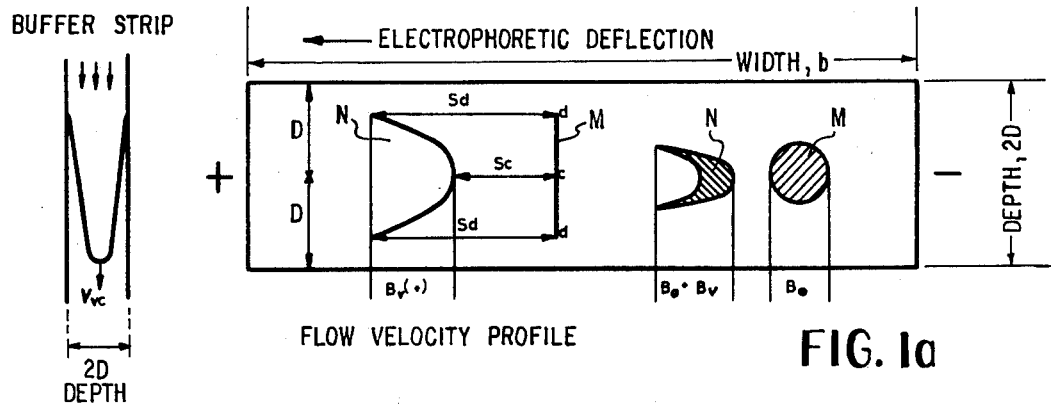
FIGS. 1a, 1b and 1c are schematic representations used to explain the influences of, respectively, the flow velocity profile, the electroosmosis effected by the zeta potential, and the temperature gradient on the cross sections of sample flow bands. Each of FIGS. 1a, 1b, and 1c includes a right-hand portion illustrating certain flow characteristics with respect to a plane perpendicular to the direction of stream flow and a left-hand portion constituting a schematic illustration in a plane parallel to the direction of stream flow.

The relationships with respect to effects (a), (b), and (c), above, are shown in FIGS. 1a, b, and c, respectively, wherein M is the original cross-section of the sample stream, which is assumed, for the purpose of the following explanations, as being linear or line - like, and N is the cross-section of the sample stream modified by the effect under consideration. Diffusion, which produces a uniform enlargement of the cross section in all transverse directions, is here to be disregarded since its influence is generally negligible and cannot be compensated by the measures taken according to the present invention.

As shown in FIG. 1a, the difference between the deflection path $S_c$ in the center, c, of the separation chamber gap and the deflection path $S_d$ at a locus of the gap at a distance d from the center of the gap can be considered the band broadening value $B_v$, where $$B_v = S_d - S_c \qquad (1)$$

Figure 2:
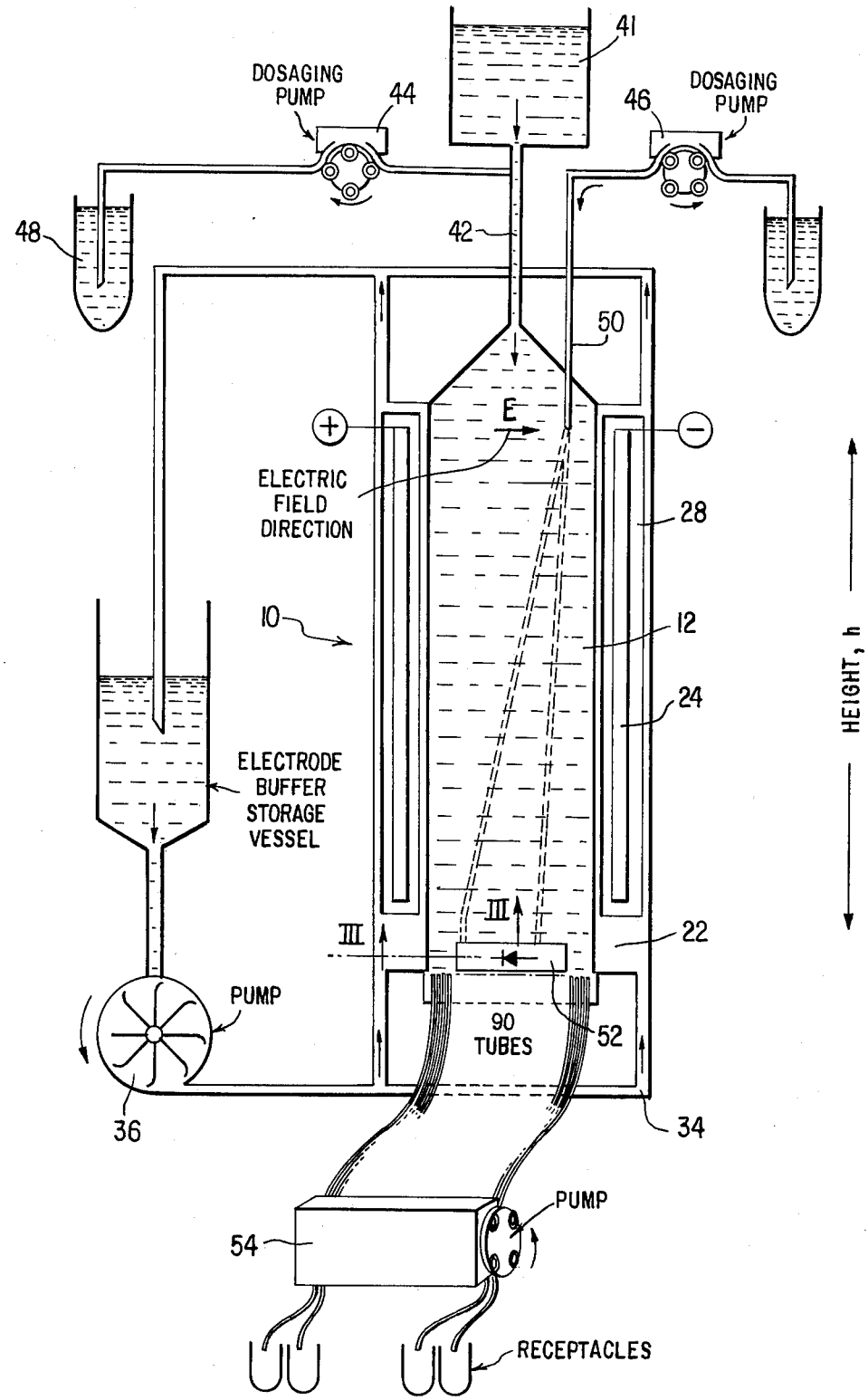
FIG. 2 is a schematic front view of one preferred embodiment of apparatus according to the invention.

The deflection paths S can generally be expressed by
$$S = h \cdot (V_e/V_v) \qquad (2)$$
where
$h =$ the length of the separating chamber in the flow direction,
i.e. in FIG. 2 between 51 and 52;
$V_e =$ effective electrophoretic mobility lateral fraction velocity, and
$V_v =$ buffer flow velocity.

Both the velocities $V_v$ and $V_e$ have the parabolic variation characteristic $$V_v = V_{vc} \cdot (1 - \frac{d^2}{D^2}) \qquad (3)$$

where
$V_{vc} =$ buffer flow velocity at the mid-depth of the buffer strip, i.e. in the center of the gap,
$D =$ one-half the gap depth, or thickness,
$d =$ distance from the center of the gap in the direction of the gap depth.

Figure 1B:
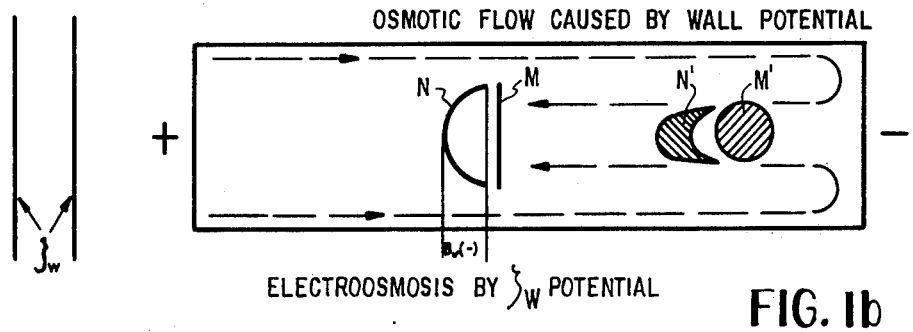

Based on these changes in the buffer flow velocity across the gap depth, there results, for $S_c - S_d$, a corresponding profile of the concentration distribution of the fraction, due to differing periods of dwell. This profile is superposed on a profile resulting from an electroosmotically-actuated wall flow or central flow component $V_w$ or $V_{oc}$, whose form is shown in FIG. 1b, which is added to the actual electrophoretic particle velocity $V_a$ ($V_a = \bar{u}_{el} \cdot E$, where $\bar{u}_{el}$ is the effective mobility and E the effective electric field intensity), such that:

$$V_e = V_{oc}(1 - \frac{d^2}{D^2}) - V_w + V_a \qquad (4)$$

The sign of $V_w$ is applicable for the usually applicable prerequisite of an identical sign for the surface potential $\zeta_w$ of chamber walls and of the particles $\zeta_a$.

The following applies for the temperature dependence of the electrophoretic deflection velocity $V_a$ with a given field intensity E across the gap width b in the presence of a temperature gradient extending transversely to the gap, in the direction of the gap depth:

$$V_a = V_{ac}(1 - \frac{K \frac{d^2}{D^2}}{1 + K}), \text{ where} \qquad (5)$$

K is the influence of temperature gradient as a function of the electric power P of the electric current with reference to the surface area $h \cdot b$ (height × width) of the separating chamber, such that:
$$K = 0.66 \, D \, (P/h.b) \qquad (6)$$

Figure 1C:
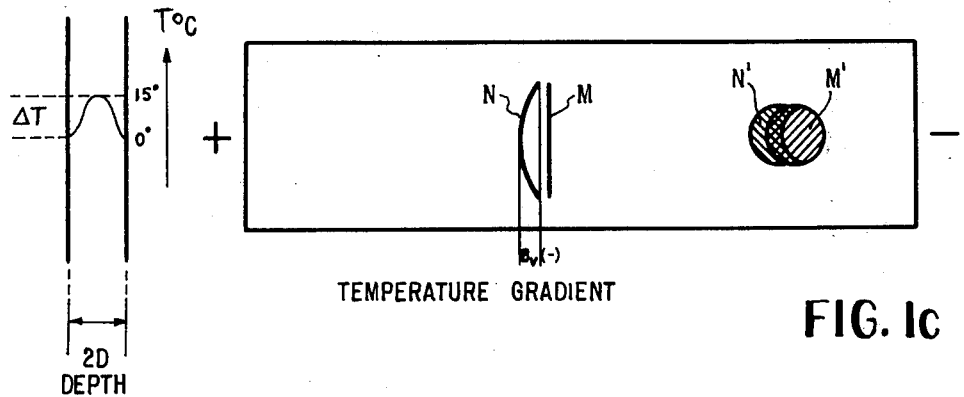

The influence of this effect is shown in FIG. 1c. Thus, a predetermined power P produces a predetermined temperature gradient $\Delta T$, a typical value being 15 ° C. A typical temperature distribution diagram is shown on the left-hand side of FIG. 1c.

A combination of equations 3, 4 and 5 produces the following expression for the deflection path of a particle under observation as a function of the distance d from the gap center in the depth direction:

$$S_d = h \frac{V_{oc}(1 - \frac{d^2}{D^2}) - V_w + V_{ac}(1 - \frac{K \frac{d^2}{D^2}}{1 + K})}{V_{vc}(1 - \frac{d^2}{D^2})} \qquad (7)$$

In the center of the gap the following applies:

$$S_c = h \frac{V_{oc} - V_w + V_{ac}}{V_{vc}} \qquad (8)$$

and for the band broadening value $B_v$, in view of equation 1, after conversion:

$$B_v = h \frac{\frac{d^2}{D^2}(\frac{V_{ac}}{1+K} - V_w)}{V_{vc}(1 - \frac{d^2}{D^2})} \qquad (9)$$

Since, as already mentioned, $V_{ac}$ is determined by the potential of particle $\zeta_a$, with respect to the medium, and $V_w$ is determined by the potential of the chamber walls, $\zeta_w$, it can be stated that:

$$B_v = h \cdot \frac{V_{ac}}{V_{vc}} \cdot (\frac{d^2}{D^2 - d^2}) \cdot (\frac{1}{1+K} - \frac{\zeta_w}{\zeta_a}) \qquad (10)$$

Equation 10 is of particular interest from the standpoint of the invention, which is concerned with reduction of band broadening. The term $$(\frac{1}{1+K} - \frac{\zeta_w}{\zeta_a}) \qquad (11)$$

shows that $B_v$ can be compensated, with a given mobility $u_a$ of the particles ($u_a = f(\zeta_a)$) by suitable selection of the separating chamber potentials $\zeta_w$ and by a suitable value for K, by employing the influence of the temperature gradient, which can be set by properly selecting the value for the power P produced by the electrical current, particularly by changes in the applied voltage and/or the conductivity of the buffer solution. In other words, with a given wall potential, the compensation can be set within certain limits by the factor K, i.e. by the electrical chamber current power or Joule heat. If $\zeta_w$ becomes equal to or greater than $\zeta_a$, there will be overcompensation in all cases.

The previous considerations were made under the assumption of a linear sample application, i.e. it was assumed that the dimension of the sample stream in the width direction of the separation gap was equal to zero.

The conditions applicable to introduction of a sample having a circular cross section in a practical experiment are shown by the cross-hatched configurations on the right of FIGS. 1a to 1c. In these FIGS. the hatched circular shape M' is the crossection of the sample stream immediately after injection, while the crescent shaped area N' is the crossection of the sample stream after transmission through the separation chamber. The dashed lines in FIG. 1b indicate the direction of the electro - osmotic flow. As can be seen very easily, the smaller the ratio of sample flow diameter, $B_o$, to gap depth, 2D, the less will be the influence of band broadening $B_v$ due to the effects listed in (a) through (c) above.

The separating chamber wall potentials $\zeta_w$ can be influenced not only by the use of known coatings on the chamber walls but also by additions to the electrolyte. For example, this can be done in a very simple manner in that a precisely set and regulated quantity of certain ions is introduced via a dosaging pump into the buffer solution which is fed into the separating chamber at one point so that the best separating effect is realized.

Various electrolytes can be added to the buffer solution to produce the ions which influence the zeta potential and/or the electrical conductivity of the buffer solution. Ions which can influence the zeta potential are, in particular, aluminum ions, barium ions, lanthanum ions and thorium ions in $10^{-4}$ to $10^{-6}$ molar solution, to name just a few examples for such ions. A suitable combination of anionic and cationic buffer substances can also be used to vary the $\zeta$ wall potential in the desired manner or to establish it. Such preferred substances are: triethanolamine - trisbuffer (tris(hydroxymethyl)-aminomethane), phosphate buffer, Hepes-(N-2-hydroxyethylpiperazine-N-ethane sulfonic acid) - borate buffer, and the like.

As regards the pH and concentration ($10^{-1} - 10^{-3}$ molar), the solutions are set to the most favorable conditions for separation. E.g. for serum albumine separation, tris-borate buffer having a pH-value 8.8 and a molar concentration of $2 \cdot 10^{-2}$ gives satisfactory results.

Figure 3:
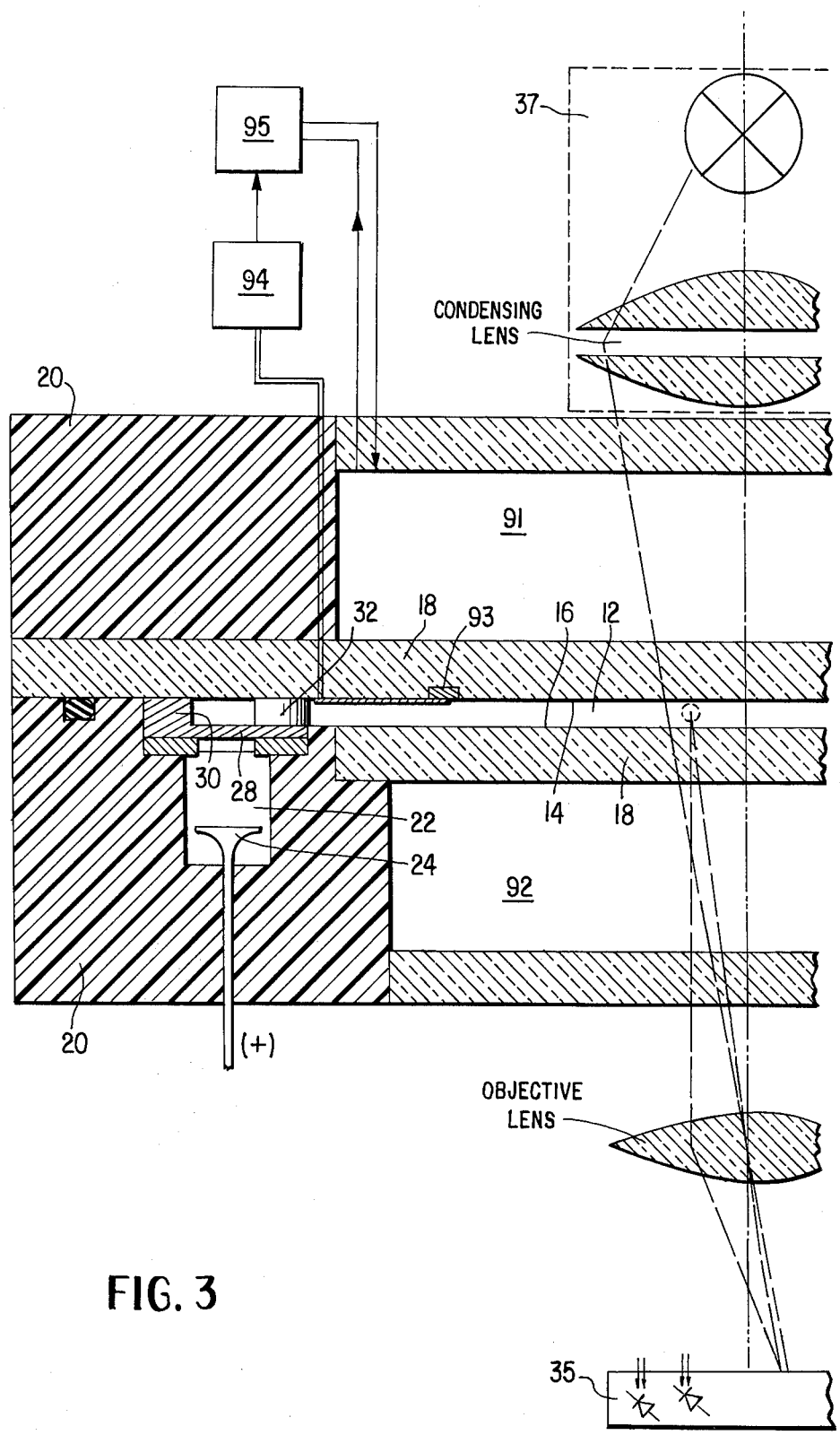
FIG. 3 is a cross-sectional view, to an enlarged scale, taken along line III—III of FIG. 2.

The apparatus which is shown schematically in FIG. 2 and in a detail cross section in FIG. 3 includes a separating chamber 10 formed to present a separating gap 12 which is delimited, as seen in FIG. 3, by two closely adjacent parallel walls 14 and 16 formed by glass plates 18 and whose spacing defines the gap depth, and by a separating chamber body 20 of insulating plastic, defining the gap width. The separating chamber body 20 includes two elongate, parallel electrode chambers 22 which each accommodate an electrode 24, connected during operation to a voltage source (not shown).

In order to separate the liquids in the electrode chambers 22 from the liquid in the separating gap 12, each chamber 22 is bounded by a membrane 28 which permits ions to pass and which do not significantly impede the flow of an electrical current. Each strip-shaped membrane 28 is provided, at the edge facing away from the separating chamber gap 12, with a sealing strip 30 and at the edge facing the separating chamber gap with a row of discrete, spaced protrusions 32 which serve as spacers and permit communication of the liquid in the separating chamber gap with the side of the membrane facing away from the electrode chamber.

The electrode chambers 22 are included in a liquid circuit 34 in which an electrolyte is circulated by a pump 36 to rinse the electrodes.

The separating chamber gap 12 is disposed in a preferably open buffer solution flow path 42 which is fed by a chamber buffer reservoir 41 and which includes a pump 44. An additional electrolyte can be selectively fed in a controlled manner into the buffer flow path 42 via a dosaging pump 44 from a further reservoir 48, or from a plurality of selectably connectable reservoirs. The separating chamber is further provided with a sample inlet 50 through which a sample substance can be introduced into the separating gap in the usual manner. The sample substance can be supplied from its own reservoir 48 by a dosaging pump 46 and exits in the form of a thin sample ribbon from an input nozzle 51 at the end of the sample inlet 50.

At the end of separating chamber 10 which is opposite the sample input there it provided an analyzer 52 which is indicated only schematically. The outlet end of chamber 10 is also provided with discharge openings for the various fractions, the openings being connected with collecting reservoirs via a further pump 54 and hoses 52a. Analyzer 52 may be designed in the usual manner and/or may include an optical detector system.

The separating chamber may be provided with an apparatus for temperature control such as is disclosed, for example, in U.S. Pat. No. 3,519,549. Thus, a fluid chamber 91 and 92 may be provided on either or both sides of the separation chamber 12. In operation, a thermistor 93 senses the temperature of the separation chamber wall 14 and controls, via a temperature regulator 94 the operation of a temperature control system 95 which circulates a cooled or heated fluid through chamber 91 and/or 92.

Since the electrode chambers 22 are each in electrical connection with the separating chamber gap 12 by means of large-area ion exchange membranes 28, the electrical parameters in the apparatus here described can be adjusted over wide limits. This and the possibility of influencing the zeta potential and/or conductivity of the buffer solution by feeding in an electrolyte by means of the arrangement 44, 48 make it possible to quickly and accurately set the operating conditions to realize optimum resolution for the desired fraction. Suitable ion exchange membranes may have a thickness of about 0.6 mm and are commercially available. A useful anion exchange membrane is comprised of copolymers of vinyl containing quaternary ammonium groups and ternary amine groups. Other satisfactory membranes are sold under the commercial names Nepton 111 PZL and Nepton 61 AZL by IONICS, Inc. Waterton, Mass.

The analyzer preferably includes a series of closely adjacent photodiodes as shown in FIG. 3 at 35. The fractions of the sample separated in the separating gap are illuminated as homogeneously as possible with the aid of a light source 37 and condenser optics 37a and the light source is focussed in the entrance pupil of an objective 37b which images the individual fractions on the photodiode arrangement 35 with as great a depth of focus as possible. Each individual photodiode is coupled to a respective corresponding stage of a shift register, if required via a keyable gating circuit, so that signals which correspond to the radiation intensity impinging on the associated photodiodes can be stored in the individual stages of the shift register. The photodiodes may be combined with the shift register into an integrated circuit, for example a charge transfer circuit.

Figure 3A:
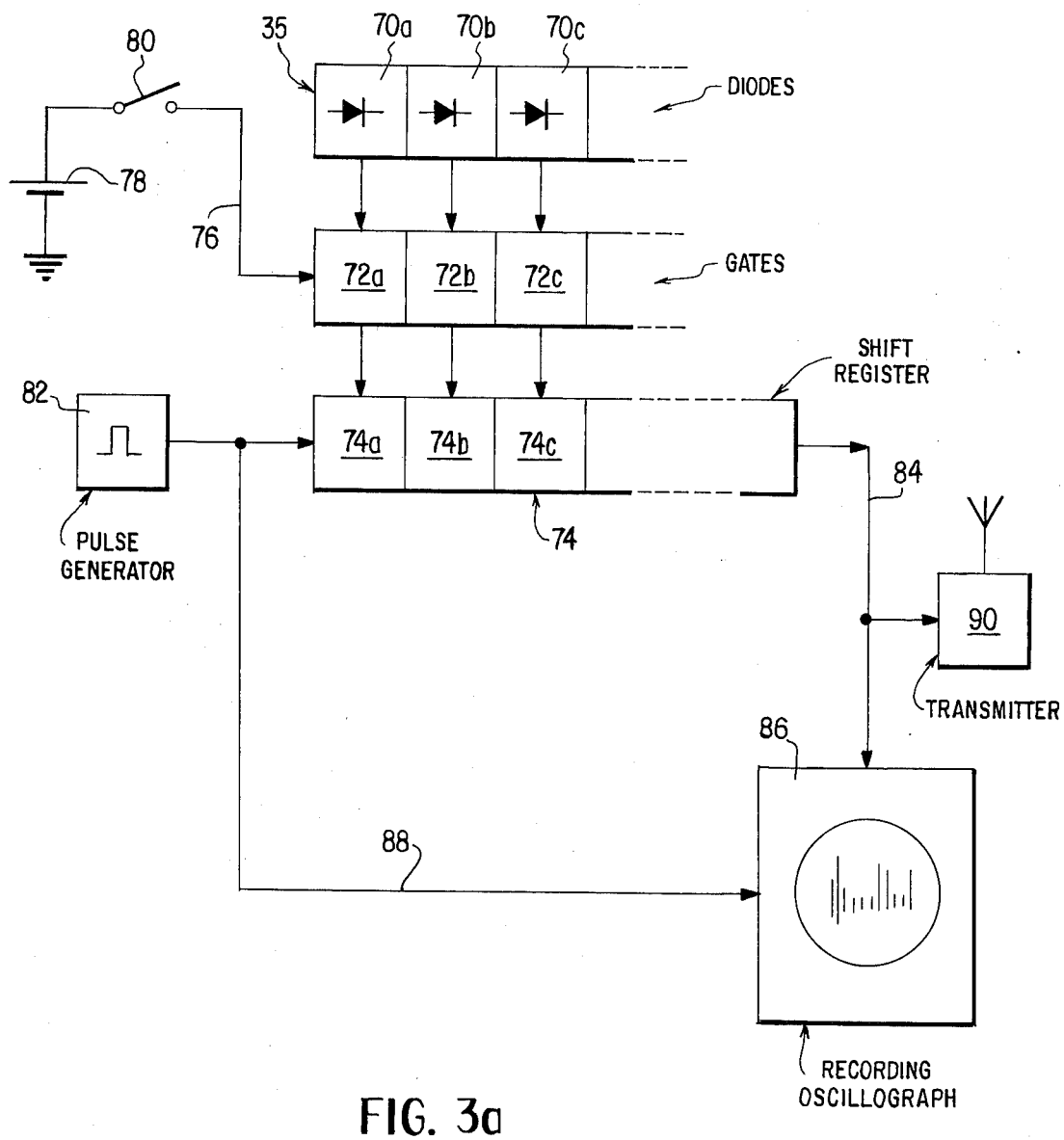
FIG. 3a is a block circuit diagram of a circuit arrangement for one member of the arrangement shown in FIG. 3.

An example of one circuit arrangement to process the signals produced by photodiode arrangement 35 is shown in FIG. 3a. Each photodiode 70a, 70b, 70c, etc. is coupled to an input of a corresponding stage 74a, 74b,... of a shift register 74 via a corresponding gating circuit 72a, 72b, 72c... All gating circuits can be enabled simultaneously in a short period of time by a gating applied via line 76 from a gating signal source which may include, for example, a voltage source 78 and a gating switch 80.

The shift register commences storing the signals from the photodiodes in the respective stages as soon as the gating circuits are enabled.

Shift register 74 is coupled to a shift pulse source 82 which can be actuated to furnish shift pulses which serially shift the information stored in stages 74a, 74b, etc., of the shift register to an output line 84. The output line 84 is coupled, for example, to a recording oscillograph 86.

In the operation of this circuit, after completion of a separation, the gating switch 80 is closed so that the shift register stages store signals which are a measure for the extinction of the radiation by the sample substances as explained above. Thereafter, switch 80 is opened and shifting pulse source 82 is actuated and the signals stored in shift register 74 are thus read out sequentially. This produces a series of pulses with amplitudes which correspond to the extinction of the respective liquid regions at the lower end of the separating chamber gap 12 between the light source 37 and the respective photodiodes 70a, 70b, etc., of the photodiode arrangement 35. This pulse series can be displayed by the memory oscillograph 86 whose abscissa scan is actuated by the first shift pulse received through a horizontal sync line 88. However, the pulse sequence can also be transmitted directly, or telemetrically, after coding, i.e. to a high frequency transmitter 90, for example, or it can be processed in any other manner.

FIG. 4 shows, as an example, the result of separation of a normal serum over four different separating times. Along the abscissa is plotted the locus of points in the separating chamber gap transversely to the flow direction and in the width direction of the gap, i.e. along the photodiode arrangement 35, and the extinctions are plotted along the ordinate.

Tris-borate buffer with a pH of 8.9, and a conductivity of 1400 $\mu$ mho/cm was used. The voltage applied to the chamber wall was 300 volts, corresponding to a measured field intensity of 105 volt/cm. A current of 165 mA was obtained, and the temperature in the center of the buffer layer in the externally cooled separating chamber was constant at $+8°$ C.

The buffer flow velocity through the separating chamber, corresponding to the varying separating periods, was varied between 1.5 and 5.0 ml/h (milliliter per hour). The serum, which was diluted with buffer in a ratio of 1:1, was introduced each time for a duration of 10 seconds. The quantity was between 0.1 and 3.1 $\mu$l (microliter), which was entirely sufficient for perfect registration.

Figure 4A:
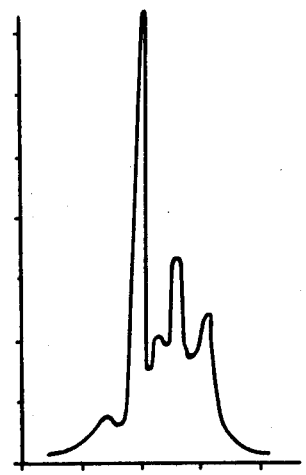
FIGS. 4a through 4d are illustrations of distribution curves obtained in practice in the separation of serum proteins.
Figure 4B:
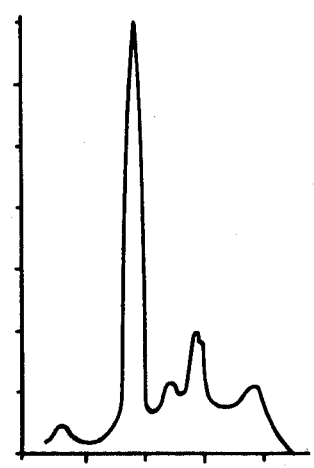
Figure 4C:
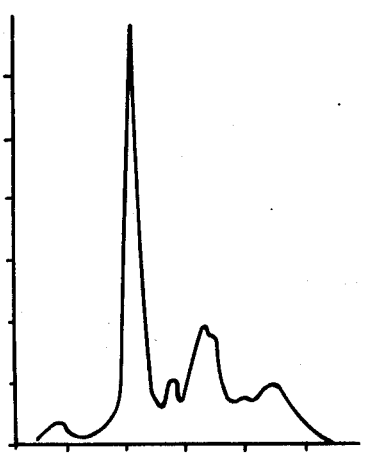
Figure 4D:
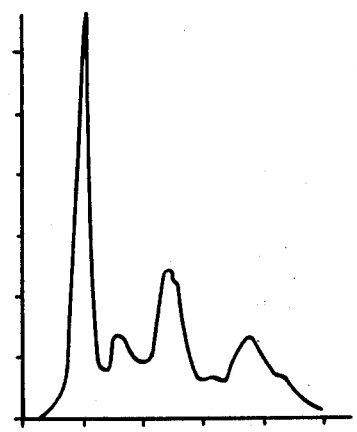

The separating periods for the distribution curves were 32 seconds for FIG. 4a, 68 seconds for FIG. 4b, 78 seconds for FIG. 4c, 106 seconds for FIG. 4d. The distribution curves were measured optically with radiation having a wavelength of 225 nm. The example shows that already after a separating period of only 32 seconds it is possible to sufficiently and evaluatably separate the serum proteins albumin, $\alpha_2$-globulin, $\beta$-globulin and $\gamma$-globulin.

In addition to the techniques disclosed above, further improvements in separation efficiency during continuous deflection electrophoresis can be achieved according to a further aspect of the present invention, by a special type of sample introduction into the separating chamber gap.

As can be easily seen, the liquid sample should be fed as accurately as possible into the center of the thin separating chamber gap, i.e. into the center between the inner walls 14 and 16 (FIG. 3). Due to the small depth d of the gap, this is, because of physical limitations, difficult to realize without interfering with the laminar flow. Furthermore, it often happens in practice, for example when the sample is introduced not exactly in the center, which may happen, even if the introduction nozzle is centered very precisely, due to adhesion of sample substance to the edge of the nozzle of the sample inlet, or as a result of an often unavoidable spiral-shaped vortex formation, that the sample ribbon comes into the vicinity of, or in contact with, the chamber walls, i.e. into a region of reduced or disappearing buffer solution flow, which results in band broadening right from the start.

Normally the diameter $B_O$ of the introduced sample flow ribbon is determined by the dosaging rate $Q_s$ of the sample and by the average velocity $v_y$ of the buffer strip. If the parabolic velocity profile of the buffer strip flow is considered, and it is required that the velocity distribution be parbolic whithin the at least initially substantially cylindrical sample ribbon, the sample ribbon diameter $B_O$ is determined from the following equation:

$$B_O = 2\sqrt{d - \sqrt{1 - \frac{Q_s}{D^2 v_y}}} \quad (12)$$

where $B_O$ is the sample ribbon diameter, in cm,
$D$ is the separating chamber gap depth, in cm,
$Q_s$ is the dosaging rate, in milliliters per hour, and
$V_y$ is the average flow velocity of the buffer film, in cm/h.

Thus, the higher the buffer flow velocity, the thinner the sample ribbon. According to this aspect of the invention, the buffer flow velocity is thus locally accelerated in the vicinity of the sample introduction location so that the sample ribbon will have a small cross section just beyond the outlet end of its input nozzle. Thus it is accomplished that the geometry and arrangement of the inlet nozzle become relatively uncritical.

In order to realize this aspect of the invention, the normally laminar buffer strip flow can be deflected by means of a suitable profile or shaped body, or by appropriate design of the separating chamber walls in the vicinity of the entrance nozzle so that due to the deflection of the flow by a profiled member or the like the desired local acceleration of the flow velocity of the buffer strip is attained.

Figure 5:
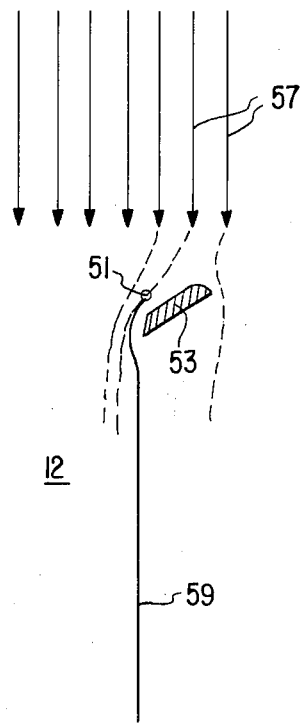
FIG. 5 is a pictorial detail view of one embodiment of a component of the apparatus of FIG. 2.
Figure 6:
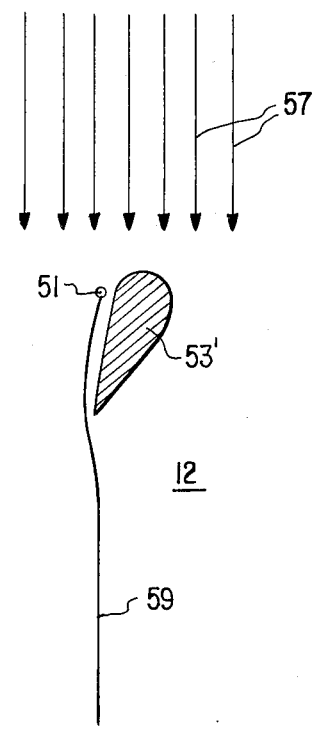
FIG. 6 is a view similar to that of FIG. 5 of another embodiment of that component.

Two embodiments of suitable profiled members or inserts to be disposed in the separating gap in the vicinity of the entrance nozzle 51 are shown in FIGS. 5 and 6, both of which are cross-sectional detail views in a direction parallel to the walls 14 and 16 in the separating gap.

FIG. 5 shows a deflector body 53 which has a flat shape and which extends in the direction of the depth of the separating gap 12, i.e. from wall 14 to wall 16. This is associated with a tube 55, shown in FIG. 7, which forms the sample inlet 50 of FIG. 2 and which, according to a further feature of the invention, passes through a glass plate 18, i.e. not as usual between the glass plates as shown in FIG. 2. The deflector body 53 constricts the flow lines 57 of the buffer stream in the vicinity of nozzle 51 so that local flow velocity accelerations result and the sample ribbon exiting from nozzle 51 has a small cross section behind the nozzle as discussed above.

FIG. 6 shows a differently shaped deflector body 53' which has an approximately tear drop shaped cross section, or the cross section of an airplane wing. It has the same effect as explained with reference to FIG. 5.

Figure 8:
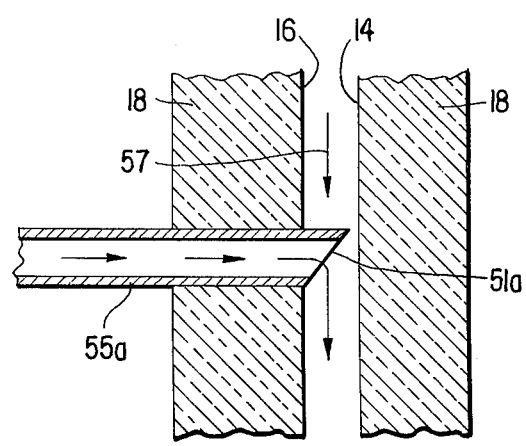

FIG. 8 shows a modified version of the entrance nozzle. Here a tube 55a is obliquely cut at its end so that the entrance nozzle 51a is directed away from the source of buffer flow.

Figure 7:
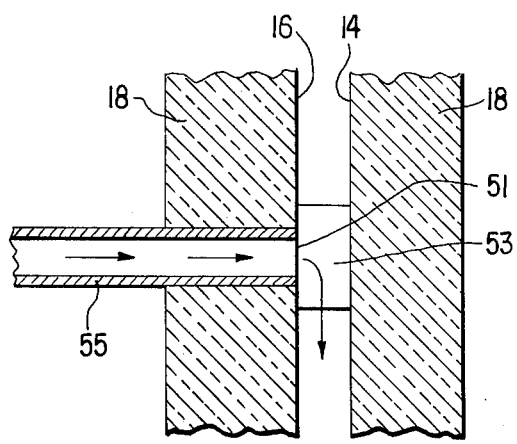
FIGS. 7 and 8 are cross-sectional, detail views of two embodiments of the portion of the apparatus of FIG. 2 associated with the components of FIGS. 5 and 6.

The types of sample introduction shown in FIGS. 7 and 8 may be used with or without the deflector bodies of FIGS. 5 and 6.

It will be understood that the above description of the present invention is susceptible to various modifications, changes and adaptations, and the same are intended to be comprehended within the meaning and the range of equivalents of the appended claims.

What is claimed is:

1. In apparatus for performing a continuous, free-film deflection electrophoresis procedure, the apparatus including: means defining a separating chamber having two spaced parallel walls delimiting opposite boundaries of a separating chamber gap, and two electrode chambers each disposed adjacent a respective opposite, lateral edge of the gap; two ion transmitting membranes each separating a respective electrode chamber from the separating chamber gap; first supply means for supplying a buffer solution to one end of the gap so that the solution flows in the form of a thin layer through the gap; second supply means disposed downstream of the first supply means for introducing into the thin buffer solution layer a spatially narrowly defined stream of a sample mixture; voltage applying means arranged to produce an electric separating field extending transversely to the direction of buffer solution flow and parallel to the two spaced walls for causing the sample stream to be divided into fractions as it traverses the length of the gap, the voltage applying means being composed of two electrodes each disposed in a respective one of the electrode chambers; and means for analyzing such fractions, the improvement wherein said apparatus comprises third supply means for introducing controlled quantities of an adjuvant fluid into the buffer solution upstream of the point of introduction of the sample mixture into the buffer solution layer, and wherein said means for analyzing comprises: a light source disposed to one side of said separating chamber gap; and a series of photodiodes disposed to the other side of said separating chamber gap and extending transversely to the direction of buffer solution flow through said gap; a shift register having a plurality of stages each operatively coupled to a respective one of said photodiodes in a manner to permit each said stage to store signals corresponding to the radiation energy impinging on the associated photodiode, and an interrogation device operatively coupled to said shift register for serially reading out such stored signals.

2. Apparatus as defined in claim 1 wherein said third supply means comprise an adjuvant fluid reservoir and a dosaging pump connected between said reservoir and the point of introduction of adjuvant fluid to the buffer solution layer.

3. Apparatus as defined in claim 2 wherein said reservoir contains an electrolyte including ions of at least one element selected from the group consisting of aluminum, barium, lanthanum and thorium.

4. Apparatus as defined in claim 1 further comprising means defining a liquid circuit containing said electrode chambers.

5. Apparatus as defined in claim 1 wherein said membranes extend substantially parallel to said separating chamber walls.

6. Apparatus as defined in claim 1 wherein said membranes are disposed substantially in the plane of one of said separating chamber walls such that one side of each said membrane is adjacent said separating chamber gap and the other side of each said membrane is adjacent its respective electrode chamber.

7. Apparatus as defined in claim 6 further comprising two sealing strips each sealing a respective membrane at the edge thereof directed away from said separating chamber gap, against the other of said separating chamber walls, and spacer means interposed between the other edge of each said membrane and said other separating chamber wall, said spacer means being formed to permit passage of liquid between said separating chamber gap and the region adjacent said membranes.

8. In apparatus for performing a continuous, free-film deflection electrophoresis procedure, the apparatus including: means defining a separating chamber having two spaced parallel walls delimiting opposite boundaries of a separating chamber gap, and two electrode chambers each disposed adjacent a respective opposite, lateral edge of the gap; two ion transmitting membranes each separating a respective electrode chamber from the separating chamber gap; first supply means for supplying a buffer solution to one end of the gap so that the solution flows in the form of a thin layer through the gap; second supply means disposed downstream of the first supply means for introducing into the thin buffer solution layer a spatially narrowly defined stream of a sample mixture; voltage applying means arranged to produce an electric separating field extending transversely to the direction of buffer solution flow and parallel to the two spaced walls for causing the sample mixture stream to be divided into fractions as it traverses the length of the gap, the voltage applying means being composed of two electrodes each disposed in a respective one of the electrode chambers; and means for analyzing such fractions, the improvement wherein said means for analyzing comprises: a light source disposed to one side of said separating chamber gap; and a series of photodiodes disposed to the other side of said separating chamber gap and extending transversely to the direction of buffer solution flow through said gap; a shift register having a plurality of stages each operatively coupled to a respective one of said photodiodes in a manner to permit each said stage to store signals corresponding to the radiation energy impinging on the associated photodiode, and an interrogation device operatively coupled to said shift register for serially reading out such stored signals.

9. An arrangement as defined in claim 8 wherein said second supply means comprises a sample line which passes through one of said separating chamber walls.

10. An arrangement as defined in claim 9 wherein said sample line is constituted by a small tube having an oblique outlet end and extending into the area between said separating chamber walls.

11. An arrangement as defined in claim 8 further comprising fluid flow modifying means disposed in said chamber for increasing the buffer solution flow velocity in the vicinity of the location at which the sample solution is fed into the buffer solution.

12. An arrangement as defined in claim 11 wherein said fluid flow modifying means comprise a fluid deflector body.

* * * * *